United States Patent

Gesing et al.

Patent Number: 5,006,156
Date of Patent: Apr. 9, 1991

[54] HERBICIDAL SULFONYLAMINOAZINES

[75] Inventors: Ernst R. Gesing, Erkrath-Hochdahl; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 439,714

[22] Filed: Nov. 20, 1989

[30] Foreign Application Priority Data

Dec. 7, 1988 [DE] Fed. Rep. of Germany ....... 3841086

[51] Int. Cl.$^5$ .................. C07D 403/04; C07D 251/46; A01N 43/66; A01N 43/68
[52] U.S. Cl. ........................................ 71/93; 544/211; 544/212; 544/206; 544/207; 544/208; 544/209
[58] Field of Search ............... 544/211, 212, 206, 207, 544/208, 209; 71/93

[56] References Cited

PUBLICATIONS

Hanagan et al., Chemical Abstracts, vol. 103, entry 178272y (1985).

Primary Examiner—John M. Ford
Attorney, Agent, or Firm—Sprung Horn Kramer & Woods

[57] ABSTRACT

Herbicidal sulphonylaminoazines of the formula

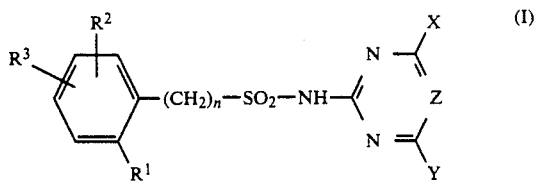

in which
$R^1$ represents halogen, cyano, nitro, $C_1$-$C_2$-alkyl, $C_1$-$C_2$-halogenoalkyl, $C_1$-$C_2$-alkoxy, $C_1$-$C_2$-halogenoalkoxy, $C_1$-$C_2$-alkylthio, $C_1$-$C_2$-halogenoalkylthio, $C_1$-$C_2$-alkylsulphinyl, $C_1$-$C_2$-halogenoalkylsulphinyl, $C_1$-$C_2$-alkylsulphonyl, $C_1$-$C_2$-halogenoalkylsulphonyl, $C_1$-$C_2$-alkoxy-$C_1$-$C_2$-alkoxy, di-($C_1$-$C_2$-alkylamino)-sulphonyl, N-($C_1$-$C_2$-alkoxy)-N-($C_1$-$C_2$-alkyl)-aminosulphonyl or $C_1$-($C_2$-alkoxy-carbonyl,
$R^2$ and $R^3$ independently of one another represent hydrogen, halogen, alkyl or halogenoalkyl,
n represents the numbers 0 or 1,
X represents hydrogen, $C_1$-$C_2$-alkyl, $C_1$-$C_2$-halogenoalkyl, $C_1$-$C_2$-alkyl, cyclopropyl, $C_1$-$C_2$-alkoxy, $C_1$-$C_2$-halogenoalkoxy, $C_1$-$C_2$-alkoxy-$C_1$-$C_2$-alkoxy, $C_1$-$C_2$-alkylthio, $C_1$-$C_2$-alkylamino or di-($C_1$-$C_2$-alkyl)-amino,
Y represents halogen, $C_1$-$C_2$-alkyl, $C_1$-$C_2$-halogenoalkyl, cyclopropyl, $C_2$-$C_2$-alkoxy, $C_1$-$C_2$-halogenoalkoxy or $C_1$-$C_2$-alkylthio and
Z represents nitrogen or a CH group,
and salts thereof.

11 Claims, No Drawings

HERBICIDAL SULFONYLAMINOAZINES

The invention relates to new sulphonylaminoazines, to processes for their preparation, and to their use as herbicides.

New sulphonylaminoazines of the general formula (I)

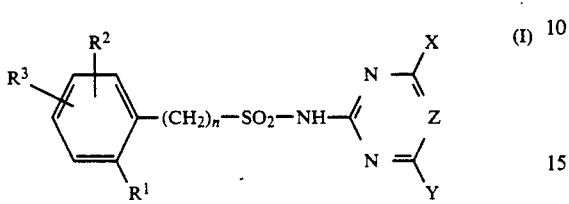

in which
R$^1$ represents halogen, cyano, nitro, C$_1$-C$_2$-alkyl, C$_1$-C$_2$-halogenoalkyl, C$_1$-C$_2$-alkoxy, C$_1$-C$_2$-halogenoalkoxy, C$_1$-C$_2$-alkylthio, C$_1$-C$_2$-halogenoalkylthio, C$_1$-C$_2$-alkylsulphinyl, C$_1$-C$_2$-halogenoalkylsulphinyl, C$_1$-C$_2$-alkylsulphonyl, C$_1$-C$_2$-halogenoalkylsulphonyl, C$_1$-C$_2$-alkoxy-C$_1$-C$_2$-alkoxy, di-(C$_1$-C$_2$-alkylamino)-sulphonyl, N-(C$_1$-C$_2$-alkoxy)-N-(C$_1$-C$_2$-alkyl)-aminosulphonyl or C$_1$-C$_2$-alkoxy-carbonyl,
R$^2$ and R$^3$ independently of one another represent hydrogen, halogen, alkyl or halogenoalkyl,
n represents the number 0 or 1,
X represents hydrogen, C$_1$-C$_2$-alkyl, C$_1$-C$_2$-halogenoalkyl, C$_1$-C$_2$-alkoxy-C$_1$-C$_2$-alkyl, cyclopropyl, C$_1$-C$_2$-alkoxy, C$_1$-C$_2$-halogenoalkoxy, C$_1$-C$_2$-alkoxy-C$_1$-C$_2$-alkoxy, C$_1$-C$_2$-alkylthio, C$_1$-C$_2$-alkylamino or di-(C$_1$-C$_2$-alkyl)-amino,
Y represents halogen, C$_1$-C$_2$-alkyl, C$_1$-C$_2$-halogenoalkyl, cyclopropyl, C$_2$-C$_2$-alkoxy, C$_1$-C$_2$-halogenoalkoxy or C$_1$-C$_2$-alkylthio and
Z represents nitrogen or a CH group, and salts of the compounds of (he formula (I) have been found.

The new sulphonylaminoazines of the general formula (I) are obtained when
(a) sulphonamides of the general formula (II)

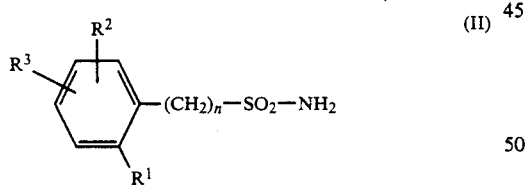

in which
R$^1$, R$^2$, R$^3$ and n have the abovementioned meanings, are reacted with azines of the general formula (III)

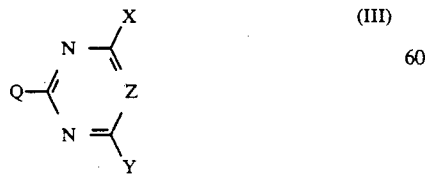

in which
X, Y and Z have the abovementioned meanings and

Q represents a nucleophilic leaving group,
if appropriate in the presence of an acid acceptor and if appropriate in the presence of a diluent, or when
(b) sulphonyl chlorides of the general formula (IV)

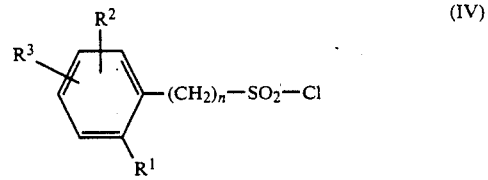

in which
R$^1$, R$^2$, R$^3$ and n have the abovementioned meanings,
are reacted with aminoazines of the general formula (V)

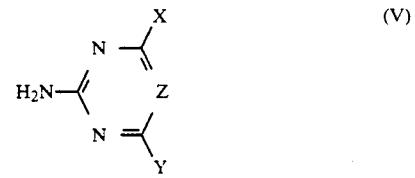

in which
X, Y and Z have the abovementioned meanings,
if appropriate in the presence of an acid acceptor and if appropriate in the presence of a diluent.

The new sulphonylaminoazines of the general formula (I) are distinguished by a powerful herbicidal activity.

The invention preferably relates to compounds of the formula (I) in which
R$^1$ represents fluorine, chlorine, bromine, iodine, cyano, nitro, methyl, trifluoromethyl, chlorodifluoromethyl, difluoromethyl, methoxy, ethoxy, difluoromethoxy, trifluoromethoxy, chlorodifluoromethoxy, 2-chloro-ethoxy, 1,1,2,2-tetrafluoroethoxy, 2-chloro-1,1,2-trifluoroethoxy, methylthio, ethylthio, difluoromethylthio, trifluoromethylthio, chlorodifluoromethylthio, methylsulphinyl, ethylsulphinyl, trifluoromethylsulphinyl, methylsulphonyl, ethylsulphonyl, trifluoromethylsulphonyl, 2-methoxy-ethoxy, 2-ethoxy-ethoxy, dimethylaminosulphonyl, N-methoxy-N-methylaminosulphonyl, methoxycarbonyl or ethoxycarbonyl,
R$^2$ and R$^3$ independently of one another represent hydrogen, fluorine, chlorine, bromine, methyl or trifluoromethyl,
n represents the number 0 or 1,
X represents hydrogen, methyl, ethyl, trifluoromethyl, chloromethyl, methoxymethyl, cyclopropyl, methoxy, ethoxy, difluoromethoxy, 2,2,2-trifluoroethoxy, methoxy-methoxy, 2-methoxy-ethoxy, methylthio, methylamino, ethylamino or dimethylamino,
Y represents fluorine, chlorine, bromine, methyl, ethyl, trifluoromethyl, chloromethyl, cyclopropyl, methoxy, ethoxy, difluoromethoxy, 2,2,2,-trifluoroethoxy or methylthio and
Z represents nitrogen or a CH group,
and the sodium and potassium salts of the compounds of the formula (I).

In particular, the invention relates to compounds of the formula (I) in which

R$^1$ represents fluorine, chlorine, bromine, methyl, trifluoromethyl, difluoromethoxy, trifluoromethoxy, 2-chloro-ethoxy, methylthio, methylsulphonyl, dimethylaminosulphonyl, methoxycarbonyl or ethoxycarbonyl, R$^2$ represents hydrogen, fluorine or chlorine, R$^3$ represents hydrogen, n represents the number 0 or 1, X represents methyl, methoxy or ethoxy, Y represents methyl, methoxy or ethoxy and Z represents nitrogen or a CH group.

Examples of the compounds of the formula (I) according to the invention are listed in Table 1 below.

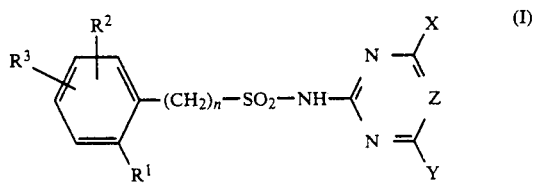

TABLE 1

Examples of the compounds of the formula (I)

| R$^1$ | R$^2$ | R$^3$ | n | X | Y | Z |
|---|---|---|---|---|---|---|
| F | H | H | 0 | CH$_3$ | CH$_3$ | CH |
| F | H | H | 0 | CH$_3$ | CH$_3$ | N |
| F | H | H | 0 | CH$_3$ | OCH$_3$ | CH |
| F | H | H | 0 | CH$_3$ | OCH$_3$ | N |
| F | H | H | 0 | CH$_3$ | OC$_2$H$_5$ | CH |
| F | H | H | 0 | CH$_3$ | OC$_2$H$_5$ | N |
| F | H | H | 0 | OCH$_3$ | OCH$_3$ | CH |
| F | H | H | 0 | OCH$_3$ | OCH$_3$ | N |
| F | H | H | 0 | OC$_2$H$_5$ | OC$_2$H$_5$ | N |
| Cl | H | H | 0 | CH$_3$ | CH$_3$ | CH |
| Cl | H | H | 0 | CH$_3$ | CH$_3$ | N |
| Cl | H | H | 0 | CH$_3$ | OCH$_3$ | CH |
| Cl | H | H | 0 | CH$_3$ | OCH$_3$ | N |
| Cl | H | H | 0 | CH$_3$ | OC$_2$H$_5$ | CH |
| Cl | H | H | 0 | CH$_3$ | OC$_2$H$_5$ | N |
| Cl | H | H | 0 | OCH$_3$ | OCH$_3$ | CH |
| Cl | H | H | 0 | OCH$_3$ | OCH$_3$ | N |
| Cl | H | H | 0 | OC$_2$H$_5$ | OC$_2$H$_5$ | N |
| Cl | H | H | 1 | OCH$_3$ | OCH$_3$ | CH |
| Cl | H | H | 1 | OCH$_3$ | OCH$_3$ | N |
| Cl | (2-)F | H | 0 | CH$_3$ | CH$_3$ | CH |
| Cl | (2-)Cl | H | 0 | CH$_3$ | CH$_3$ | CH |
| Br | H | H | 0 | CH$_3$ | CH$_3$ | CH |
| Br | H | H | 0 | CH$_3$ | CH$_3$ | N |
| Br | H | H | 0 | CH$_3$ | OCH$_3$ | CH |
| Br | H | H | 0 | CH$_3$ | OCH$_3$ | N |
| Br | H | H | 0 | OCH$_3$ | OCH$_3$ | CH |
| Br | H | H | 0 | OCH$_3$ | OCH$_3$ | N |
| Br | H | H | 0 | OC$_2$H$_5$ | OC$_2$H$_5$ | N |
| CF$_3$ | H | H | 0 | CH$_3$ | CH$_3$ | CH |
| CF$_3$ | H | H | 0 | CH$_3$ | CH$_3$ | N |
| CF$_3$ | H | H | 0 | CH$_3$ | OCH$_3$ | CH |
| CF$_3$ | H | H | 0 | CH$_3$ | OCH$_3$ | N |
| CF$_3$ | H | H | 0 | OCH$_3$ | OCH$_3$ | CH |
| CF$_3$ | H | H | 0 | OCH$_3$ | OCH$_3$ | N |
| CF$_3$ | H | H | 0 | OC$_2$H$_5$ | OC$_2$H$_5$ | N |
| OCHF$_2$ | H | H | 0 | CH$_3$ | CH$_3$ | CH |
| OCHF$_2$ | H | H | 0 | CH$_3$ | CH$_3$ | N |
| OCHF$_2$ | H | H | 0 | CH$_3$ | OCH$_3$ | CH |
| OCHF$_2$ | H | H | 0 | CH$_3$ | OCH$_3$ | N |
| OCHF$_2$ | H | H | 0 | OCH$_3$ | OCH$_3$ | CH |
| OCHF$_2$ | H | H | 0 | OCH$_3$ | OCH$_3$ | N |
| OCHF$_2$ | H | H | 0 | OC$_2$H$_5$ | OC$_2$H$_5$ | N |
| OCF$_3$ | H | H | 0 | CH$_3$ | CH$_3$ | CH |
| OCF$_3$ | H | H | 0 | CH$_3$ | CH$_3$ | N |
| OCF$_3$ | H | H | 0 | CH$_3$ | OCH$_3$ | CH |
| OCF$_3$ | H | H | 0 | CH$_3$ | OCH$_3$ | N |
| OCF$_3$ | H | H | 0 | OCH$_3$ | OCH$_3$ | CH |
| OCF$_3$ | H | H | 0 | OCH$_3$ | OCH$_3$ | N |
| OCF$_3$ | H | H | 0 | OC$_2$H$_5$ | OC$_2$H$_5$ | N |

TABLE 1-continued

Examples of the compounds of the formula (I)

| R$^1$ | R$^2$ | R$^3$ | n | X | Y | Z |
|---|---|---|---|---|---|---|
| OCH$_2$CH$_2$Cl | H | H | 0 | CH$_3$ | OCH$_3$ | CH |
| OCH$_2$CH$_2$Cl | H | H | 0 | CH$_3$ | OCH$_3$ | N |
| OCH$_2$CH$_2$Cl | H | H | 0 | OCH$_3$ | OCH$_3$ | CH |
| OCH$_2$CH$_2$Cl | H | H | 0 | OCH$_3$ | OCH$_3$ | N |
| SCH$_3$ | H | H | 0 | CH$_3$ | CH$_3$ | CH |
| SCH$_3$ | H | H | 0 | CH$_3$ | CH$_3$ | N |
| SCH$_3$ | H | H | 0 | CH$_3$ | OCH$_3$ | CH |
| SCH$_3$ | H | H | 0 | CH$_3$ | OCH$_3$ | N |
| SCH$_3$ | H | H | 0 | OCH$_3$ | OCH$_3$ | N |
| SO$_2$CH$_3$ | H | H | 0 | CH$_3$ | CH$_3$ | CH |
| SO$_2$CH$_3$ | H | H | 0 | CH$_3$ | CH$_3$ | N |
| SO$_2$CH$_3$ | H | H | 0 | CH$_3$ | OCH$_3$ | CH |
| SO$_2$CH$_3$ | H | H | 0 | CH$_3$ | OCH$_3$ | N |
| SO$_2$CH$_3$ | H | H | 0 | OCH$_3$ | OCH$_3$ | N |
| SO$_2$N(CH$_3$)$_2$ | H | H | 0 | CH$_3$ | CH$_3$ | CH |
| SO$_2$N(CH$_3$)$_2$ | H | H | 0 | CH$_3$ | CH$_3$ | N |
| SO$_2$N(CH$_3$)$_2$ | H | H | 0 | CH$_3$ | OCH$_3$ | CH |
| SO$_2$N(CH$_3$)$_2$ | H | H | 0 | CH$_3$ | OCH$_3$ | N |
| SO$_2$N(CH$_3$)$_2$ | H | H | 0 | OCH$_3$ | OCH$_3$ | CH |
| SO$_2$N(CH$_3$)$_2$ | H | H | 0 | OCH$_3$ | OCH$_3$ | N |
| SO$_2$N(CH$_3$)$_2$ | H | H | 0 | OC$_2$H$_5$ | OC$_2$H$_5$ | N |
| COOCH$_3$ | H | H | 0 | CH$_3$ | CH$_3$ | CH |
| COOCH$_3$ | H | H | 0 | CH$_3$ | CH$_3$ | N |
| COOCH$_3$ | H | H | 0 | CH$_3$ | OCH$_3$ | CH |
| COOCH$_3$ | H | H | 0 | CH$_3$ | OC$_2$H$_5$ | CH |
| COOCH$_3$ | H | H | 0 | CH$_3$ | OCH$_3$ | N |
| COOCH$_3$ | H | H | 0 | CH$_3$ | OC$_2$H$_5$ | N |
| COOCH$_3$ | H | H | 0 | OCH$_3$ | OCH$_3$ | CH |
| COOCH$_3$ | H | H | 0 | OCH$_3$ | OCH$_3$ | N |
| COOCH$_3$ | H | H | 0 | OC$_2$H$_5$ | OC$_2$H$_5$ | CH |
| COOCH$_3$ | H | H | 0 | OC$_2$H$_5$ | OC$_2$H$_5$ | N |
| COOC$_2$H$_5$ | H | H | 0 | CH$_3$ | CH$_3$ | CH |
| COOC$_2$H$_5$ | H | H | 0 | CH$_3$ | CH$_3$ | N |
| COOC$_2$H$_5$ | H | H | 0 | CH$_3$ | OCH$_3$ | CH |
| COOC$_2$H$_5$ | H | H | 0 | CH$_3$ | OCH$_3$ | N |
| COOC$_2$H$_5$ | H | H | 0 | OCH$_3$ | OCH$_3$ | CH |
| COOC$_2$H$_5$ | H | H | 0 | OCH$_3$ | OCH$_3$ | N |
| COOCH$_3$ | H | H | 1 | OCH$_3$ | OCH$_3$ | CH |
| COOCH$_3$ | H | H | 1 | OCH$_3$ | OCH$_3$ | N |
| OCHF$_2$ | H | H | 1 | OCH$_3$ | OCH$_3$ | CH |
| OCHF$_2$ | H | H | 1 | OCH$_3$ | OCH$_3$ | N |
| OCF$_3$ | H | H | 1 | OCH$_3$ | OCH$_3$ | CH |
| OCF$_3$ | H | H | 1 | OCH$_3$ | OCH$_3$ | N |
| CH$_3$ | (6-)Cl | H | 0 | OCH$_3$ | OCH$_3$ | N |

If, for example, 2-fluoro-benzenesulphonamide and 2-chloro-4,6-dimethoxy-s-triazine are used as starting materials in process (a) according to the invention, the course of the reaction can be outlined by the following equation:

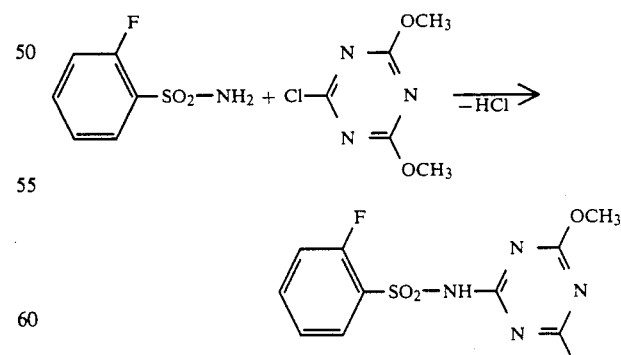

If, for example, 2-chloro-benzenesulphonyl chloride and 2-amino-4,6-dimethyl-pyrimidine are used as starting materials in process (b) according to the invention, the course of the reaction can be outlined by the following equation:

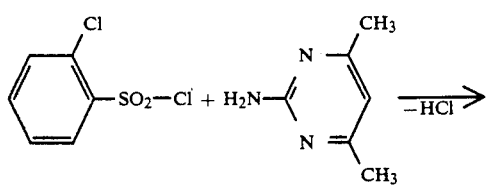

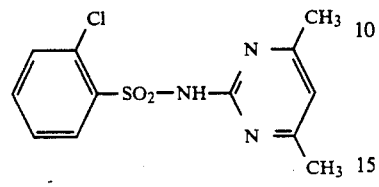

Formula (II) provides a general definition of the sulphonamides to be used as starting materials in process (a) according to the invention for the preparation of compounds of the formula (I)

In formula (II), $R^1$, $R^2$, $R^3$ and n preferably, or in particular, have those meanings which have already been mentioned above in connection with the description of the compounds of the formula (I) according to the invention as being preferred, or particularly preferred, for $R^1$, $R^2$, $R^3$ and n.

Examples of the starting materials of the formula (II) which may be mentioned are: 2-fluoro-, 2-chloro-, 2-bromo-, 2,6-dichloro-, 2-chloro6-fluoro-, 2-trifluoromethyl-, 2-difluoromethoxy-, 2-trifluoromethoxy-, 2-(2-chloro-ethoxy)-, 2-methylthio-, 2-methylsulphonyl-,2-dimethylaminosulphonyl-,2-methoxycarbonyl - and 2-ethoxycarbonyl-benzenesulphonamide and (2-chloro-phenyl)-, (2-difluoromethoxy-phenyl)-, (2-trifluoromethoxy-phenyl)-and(2-methoxycarbonyl-phenyl)methanesulphonamide.

The starting materials of the formula (II) are known and/or can be prepared by processes which are known per se (cf. J. Org. Chem. 27 (1962), 1703-1709; U.S. Pat. No. 4,371,391; U.S. Pat. No. 4,310,346; U.S. Pat. No. 4,452,628; EP-A 44,808; EP-A 87,780; U.S. Pat. No. 4,732,711; EP-A 271,780).

Formula (III) provides a general definition of the azines also to be used as starting materials in process (a) according to the invention.

In formula (III), X, Y and Z preferably, or in particular, have those meanings which have already been mentioned above in connection with the description of the compounds of the formula (I) according to the invention as being preferred, or particularly preferred, for X, Y and Z, and Q preferably represents fluorine, chlorine, methoxy, ethoxy, methylthio, ethylthio or benzylthio, or represents the group

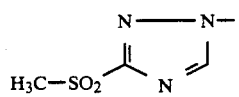

(3-methylsulphdnyl-1,2,4-triazol-1-yl); the particularly preferred leaving group Q is the last-mentioned 3-methylsulphonyl-1,2,4-triazol-1-yl group.

Examples of the starting materials of the formula (III) which may be mentioned are: 2-(3-methylsulphonyl-1,2,4-triazol-1-yl)-4,6-dimethylpyrimidine, -4-methoxy-6-methyl-pyrimidine, -4,6-dimethoxy-pyrimidine, -4-ethoxy-6-methyl-pyrlmidine, -4,6-diethoxy-pyrimidine, -4,6-dimethyl-s-triazine, -4-methoxy-6-methyl-s-triazine, -4,6-dimethoxy-s-triazine, -4-ethoxy-6-methyl-s-triazine and -4,6-diethoxy-s-triazine.

Some of the starting materials of the formula (III) are known (cf. J. Chem. Soc. 1957, 1830, 1833; J. Org. Chem. 26 (1961), 792; U.S. Pat. No. 3,308,119; U.S. Pat. No. 4,711,959).

New starting materials are those of the formula (IIIa)

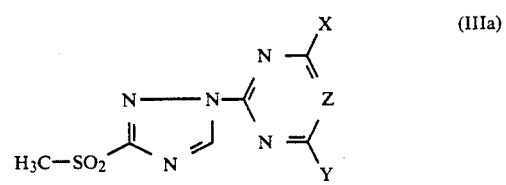

in which

X, Y and Z have the abovementioned meanings.

The new 2-(3-methylsulphonyl-1,2,4-triazol-1-yl)azines of the formula (IIIa) are obtained when azines of the formula (IIIb)

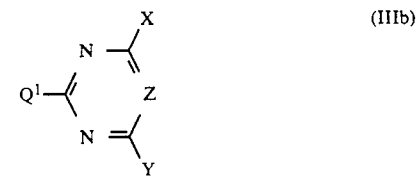

in which

X, Y and Z have the abovementioned meanings and $Q^1$ represents chlorine or methylsulphonyl, are reacted with 3-methylthio-1,2,4-triazole of the formula (VI)

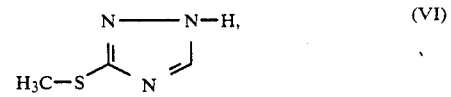

if appropriate in the presence of an acid acceptor, such as, for example, potassium carbonate, and in the presence of a diluent, such as, for example, acetonitrile or dlmethylformamide, at temperatures between 0° C. and 150° C., and the resulting 2-(3-methylthio-1,2,4-triazol-1-yl)-azines of the formula (IIIc)

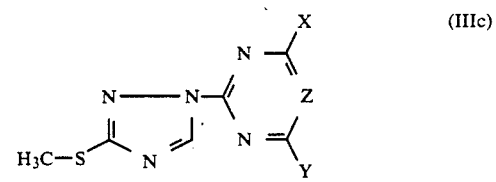

are reacted with an oxidant, such as, for example,
(a) formic acid/hydrogen peroxide, if appropriate in the presence of a catalyst, such as, for example, ammonium molybdate, and in the presence of a diluent, such as, for example, methylene chloride and water, or
(b) chlorine in the presence of a diluent, such as, for example, chloroform and water, at temperatures between −20° C. and +50° C.

In formulae (IIIa), (IIIb) and (IIIc), X, Y and Z preferably, or in particular, have those meanings which have already been mentioned above in connection with the description of the compounds of the formula (I) according to the invention as being preferred, or particularly preferred, for X, Y and Z.

Process (a) according to the invention for the preparation of the new sulphonylaminoazines of the formula (I) is preferably carried out using diluents.

Suitable diluents for this purpose are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in process (a) according to the invention are all acid-binding agents which can customarily be used for reactions of this type. Alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate, potassium carbonate, sodium tert-butoxide and potassium tert-butoxide, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO), are preferably suitable.

When carrying out process (a) according to the invention, the reaction temperatures can be varied within a relatively wide range. In general, the process is carried out at temperatures between 0° C. and 150° C., preferably at temperatures between 20° C. and 100° C.

Process (a) according to the invention is generally carried out under atmospheric pressure. However, it is also possible to carry out the process under increased or reduced pressure.

For carrying out process (a) according to the invention, the starting materials required in each case are generally employed in approximately equimolar amounts. However, it is also possible to employ one of the components employed in each case in a relatively large excess. In general, the reactions are carried out in a suitable diluent in the presence of an acid acceptor, and the reaction mixture is stirred for several hours at the specific temperature required. Working-up in process (a) according to the invention is carried out in each case by customary methods.

Formula (IV) provides a general definition of the sulphonyl chlorides to be used as starting materials in process (b) according to the invention for the preparation of compounds of the formula (I).

In formula (IV), $R^1$, $R^2$, $P^3$ and n preferably, or in particular, have those meanings which have already been mentioned above in connection with the description of the compounds of the formula (I) according to the invention as being preferred, or particularly preferred, for $R^1$, $R^2$, $R^3$ and n.

Examples of the starting materials of the formula (IV) which may be mentioned are: 2-fluoro-, 2-chloro-, 2-bromo-, 2,6-dichloro-, 2-chloro6-fluoro-, 2-trifluoromethyl-, 2-difluoromethoxy-, 2-trifluoromethoxy-, 2-(2-chloro-ethoxy)-, 2-methylthio-, 2-methylsulphonyl-,2-dimethylaminosulphonyl-,2-methoxycarbonyl- and 2-ethoxycarbonyl-benzenesulphonamide, and (2-chloro-phenyl)-, (2-difluoromethoxy-phenyl)-, (2-trifluoromethoxy-phenyl)-and(2-methoxycarbonylphenyl)methanesulphonyl chloride.

The starting materials of the formula (IV) are known and/or can be prepared by processes known per se (cf. J. Org. Chem. 33 (1968), 2104; J. Org. Chem. 25 (1960), 1824; DE-AS (German Published Specification) 2,308,262; EP-A 23,141; EP-A 23,422; EP-A 35,893; EP-A 48,143; EP-A 51,466; EP-A 64,322; EP-A 70,041; EP-A 44,808; U.S. Pat. No. 2,929,820; U.S. Pat. No. 4,282,242; U.S. Pat. No. 4,348,220; U.S. Pat. No. 4,372,778).

Formula (V) provides a general definition of the amino azines also to be used as starting materials in process (b) according to the invention.

In formula (V), X, Y and Z preferably, or in particular, have those meanings which have already been mentioned above in connection with the description of the compounds of the formula (I) according to the invention as being preferred, or particularly preferred, for X, Y and Z.

Examples of the starting materials of the formula (V) which may be mentioned are: 2-amino-4,6-dimethylpyrimidine, -4-methoxy-6-methylpyrimidine, -4,6-dimethoxy-pyrimidine, -4-ethoxy-6-methyl-pyrimidine, -4,6-diethoxy-pyrimidine, -4,6-dimethyl-s-triazine, -4-methoxy-6-methyl-s-triazine, -4,6-dimethoxy-s-triazine, -4-ethoxy-6-methyl-s-triazine and -4,6-diethoxy-s-triazine.

The starting materials of the formula (V) are known and/or can be prepared by processes known per se (cf. Chem. Pharm. Bull. 11 (1963), 1382–1388; J. Chem. Soc. 1946, 81; US Pat. No. 4,299,960).

Process (b) according to the invention is preferably carried out using diluents. Particularly suitable solvents are the same ones which have been indicated above in the case of process (a) according to the invention.

Acid acceptors which can be employed in process (b) according to the invention are all acid-binding agents which can customarily be used for reactions of this type. Preferred possible acid-binding agents are the same ones which have been indicated above in the case of process (a) according to the invention.

When carrying out process (b) according to the invention, the reaction temperatures can be varied within a relatively wide range. In general, the process is carried out at temperatures between −30° C. and +80° C., preferably at temperatures between 0° C. and 50° C.

Process (b) according to the invention is generally carried out under atmospheric pressure. However, it is also possible to carry out the process under increased or reduced pressure.

For carrying out process (b) according to the invention, the starting materials required in each case are generally employed in approximately equimolar amounts. However, it is also possible to use one of the components employed in each case in a relatively large excess. In general, the reactions are carried out in a suitable diluent in the presence of an acid acceptor, and the reaction mixture is stirred for several hours at the specific temperature required. Working-up in process (b) according to the invention is carried out in each case by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention ar particularly suitable for selectively combating dicotyledon weeds in monocotyledon crops, especially using the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foamforming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and grOund synthetic minerals, such as highly disperse silica, alumina and silicates, as solid carriers for granulas there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N,-dimethylurea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-triazin-5(4H)-one (METRIBUZIN) for combating weeds in soy beans; furthermore also 2,4-dichlorophenoxyacetic acid (2,4-D); 4-(2,4-dichlorophenoxy)-butyric acid (2,4-DB]; 2,4-dichlorophenoxypropionic acid (2,4-DP); 2-chloro-4-ethylamino-6-isopropylamino-1,3,5-triazine(ATRA- ZIN); 3-isopropyl-2,1,3-benzothiadiazin-4-one 2,2-dioxide (BENTAZONE); methyl 5-(2,4-dichlorophenoxy]-2-nitrobenzoate (BIFENOX); 3,5-dibromo-4-hydroxybenzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-chloro-4-ethylamino-6-(3-cyanopropylamino) -1,3,5-triazine(CYANAZIN); 2-[4-(2,4-dichlorophenoxy)-phenoxy]-propionic acid, its methyl ester or its ethyl ester (DICLOFOP); 4-amino-6-t-butyl3-ethylthio-1,2,4-triazin-5(4H)-one(ETHIOZIN);2-{4-[(6-chloro -2-benzoxazolyl)-oxy]-phenoxy}-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); methyl 2-[4,5-dihydro-4-methyl-4-(1-methylethyl)-5-oxo-1H-imidazol -2-yl]-4(5)-methylbenzoate(IMAZAMETHABENZ);3,5-diiod-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-{[[((4-methoxy-6-methyl-1,3,5-triazin-2-yl)-amino)-carbonyl]amino]-sulphonyl}-benzoic acid or its methyl ester (METSULFURON); N-(1-ethylpropyl)-3,4-dimethyl-2,6-dinitroaniline (PENDIMETHALIN); 0-(6-chloro-3-phenylpyridazin-4-yl) S-octyl thiocarbonate (PYRIDATE); 4-ethylamino-2-t-butylamino-6-methylthio-s-triazine (TERBUTRYNE), methyl 3-[[[[(4-methoxy-6-methyl-1,3,5-triazin-2-yl)-amino]-carbonyl]-amino]-sulphonyl]-thiophene-2-carboxylate (THIACARBURON) and methyl 3-[[[[(4-methoxy-6-methyl-1,3,5-triazin-2-yl)-amino]-carbonyl]amino]-sulphonyl]-thiophene-2-carboxylate (THIAMETURON). Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes, and granules. The application is carried out in the usual manner for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLES

EXAMPLE 1

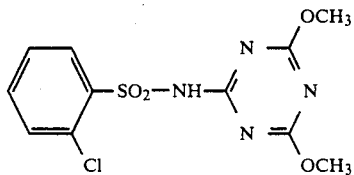

(Process (a))

A mixture of 1.43 g (5 mmol) of 2-(3-methylsulphonyl-1,2,4-triazol-1-yl)-4,6-dimethoxy-s-triazine, 0.96 g (5 mmol) of 2-chloro-benzenesulphonamide, 1.38 g (10 mmol) of potassium carbonate and 30 ml of acetonitrile is refluxed for 12 hours. The mixture is subsequently evaporated, the residue is taken up in 100 ml of water; and a pH of 1.5 is established using concentrated hydrochloric acid. The mixture is extracted three times using 50 ml of methylene chloride each time, and the combined extraction solutions are dried using sodium sulphate and filtered. The solvent is carefully removed from the filtrate by distillation under a waterpump vacuum.

0.93 g (57 % of theory) of 2-(2-chloro-phenylsulphonylamino)-4,6-dimethoxy-s-triazine are obtained as a crystalline residue of melting point 137° C.

The compounds of the formula (I) which are listed in Table 2 below can be prepared in analogy with Example 1 and in accordance with the general description of the preparation processes according to the invention.

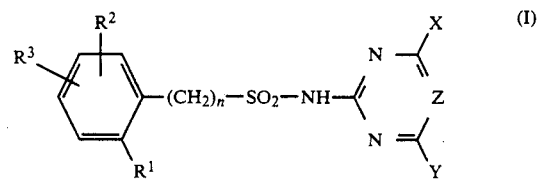

TABLE 2

| Example No. | R¹ | R² | R³ | n | X | Y | Z | Melting point |
|---|---|---|---|---|---|---|---|---|
| 2 | $CH_3$ | (6-)Cl | H | 0 | $OCH_3$ | $OCH_3$ | N | 182° C. |
| 3 | $COOCH_3$ | H | H | 0 | $OCH_3$ | $OCH_3$ | N | 150° C. |
| 4 | F | H | H | 0 | $OCH_3$ | $OCH_3$ | N | 150° C. |
| 5 | Cl | H | H | 0 | $OC_2H_5$ | $OC_2H_5$ | N | 114° C. |
| 6 | Br | H | H | 0 | $OC_2H_5$ | $OC_2H_5$ | N | 134° C. |
| 7 | F | H | H | 0 | $OC_2H_5$ | $OC_2H_5$ | N | 112° C. |
| 8 | $CO_2CH_3$ | H | H | 0 | $OC_2H_5$ | $OC_2H_5$ | N | 139° C. |
| 9 | $SO_2N(CH_3)_2$ | H | H | 0 | $OC_2H_5$ | $OC_2H_5$ | N | 124° C. |
| 10 | $CF_3$ | H | H | 0 | $OC_2H_5$ | $OC_2H_5$ | N | 153° C. |
| 11 | $CH_3$ | (6-)Cl | H | 0 | $OC_2H_5$ | $OC_2H_5$ | N | 126° C. |
| 12 | $OCHF_2$ | H | H | 0 | $OC_2H_5$ | $OC_2H_5$ | N | 148° C. |

TABLE 2-continued

Examples of the compounds of the formula (I)

| Example No. | R¹ | R² | R³ | n | X | Y | Z | Melting point |
|---|---|---|---|---|---|---|---|---|
| 13 | Cl | (6-)Cl | H | 0 | $OC_2H_5$ | $OC_2H_5$ | N | 165° C. |
| 14 | Br | H | H | 0 | $OCH_3$ | $OCH_3$ | CH | 75° C. |
| 15 | F | H | H | 0 | $CH_3$ | $CH_3$ | CH | 248° C.* |
| 16 | Cl | H | H | 0 | $CH_3$ | $CH_3$ | CH | 180° C.* |
| 17 | Br | H | H | 0 | $CH_3$ | $CH_3$ | CH | 175° C.* |
| 18 | $OCHF_2$ | H | H | 0 | $CH_3$ | $CH_3$ | CH | 247° C.* |
| 19 | Cl | (6-)Cl | H | 0 | $CH_3$ | $CH_3$ | CH | >250° C.* |
| 20 | $SO_2N(CH_3)_2$ | H | H | 0 | $CH_3$ | $CH_3$ | CH | 173° C.* |
| 21 | $COOCH_3$ | H | H | 0 | $CH_3$ | $CH_3$ | CH | 155° C.* |
| 22 | Cl | H | H | 0 | H | $CH_3$ | CH | 209° C.* |
| 23 | F | H | H | 0 | $CH_3$ | $CH_3$ | CH | 183° C. |
| 24 | Cl | H | H | 0 | $CH_3$ | $CH_3$ | CH | 217° C. |
| 25 | Br | H | H | 0 | $CH_3$ | $CH_3$ | CH | 211° C. |
| 26 | $OCF_3$ | H | H | 0 | $CH_3$ | $CH_3$ | CH | 174° C. |
| 27 | $OCHF_2$ | H | H | 0 | $CH_3$ | $CH_3$ | CH | 162° C. |
| 28 | Cl | (6-)Cl | H | 0 | $CH_3$ | $CH_3$ | CH | >250° C. |
| 29 | $SO_2N(CH_3)_2$ | H | H | 0 | $CH_3$ | $CH_3$ | CH | 163° C. |
| 30 | Cl | (6-)Cl | H | 1 | $CH_3$ | $CH_3$ | CH | 206° C. |
| 31 | $COOCH_3$ | H | H | 0 | $CH_3$ | $CH_3$ | CH | 137° C. |
| 32 | F | H | H | 0 | H | $CH_3$ | CH | 228° C. |
| 33 | Cl | H | H | 0 | H | $CH_3$ | CH | >250° C. |
| 34 | Br | H | H | 0 | H | $CH_3$ | CH | >250° C. |
| 35 | $OCF_3$ | H | H | 0 | H | $CH_3$ | CH | 241° C. |
| 36 | Cl | H | H | 0 | $CH_3$ | $OCH_3$ | CH | 163° C. |
| 37 | $COOCH_3$ | H | H | 1 | $CH_3$ | $CH_3$ | CH | 164° C. |
| 38 | Cl | H | H | 1 | $CH_3$ | $CH_3$ | CH | 163° C. |
| 39 | $OCF_3$ | H | H | 1 | $CH_3$ | $CH_3$ | CH | 134° C. |
| 40 | $COOC_2H_5$ | H | H | 0 | $CH_3$ | $CH_3$ | CH | 97° C. |
| 41 | $CH_3$ | (6-)Cl | H | 0 | $CH_3$ | $CH_3$ | CH | >250° C. |
| 42 | Cl | (4-)Cl | H | 0 | $CH_3$ | $CH_3$ | CH | >250° C. |
| 43 | $SO_2N(CH_3)_2$ | H | H | 0 | H | $CH_3$ | CH | 188° C. |
| 44 | $CH_3$ | (6-)Cl | H | 0 | H | $CH_3$ | CH | >250° C. |
| 45 | $COOCH_3$ | H | H | 1 | H | $CH_3$ | CH | 164° C. |

*Sodium salt

STARTING MATERIALS OF THE FORMULA (IIIa)

EXAMPLE (IIIa-1)

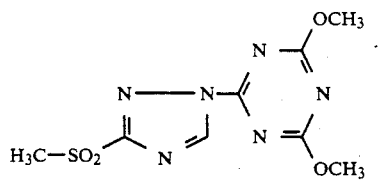

6.6 g of 30% strength hydrogen peroxide solution (in water) (0.058 mol) are added dropwise at 15° C. to 30° C. with stirring to a mixture of 3.8 g (0.015 mol) of 2-(3-methylthio-1,2,4-triazol-l-yl)-4,6-dimethoxy-s-triazine, 1.75 g (0.038 mol) of formic acid, 0.1 g of ammonium molybdate tetrahydrate and 30 ml of methylene chloride. The reaction mixture is stirred for 15 hours at 20° C., and then diluted with methylene chloride and water and shaken. The organic phase is separated off and washed with sodium hydrogen sulphite solution, then with potassium carbonate solution and finally with water, and dried with sodium sulphate and filtered. The solvent is carefully removed from the filtrate by distillation under a waterpump vacuum.

2.8 g (67% of theory) of 2-(3-methylsulphonyl-1,2,4-triazol-l-yl)-4,6-dimethoxy-s-triazine are obtained as a crystalline residue of melting point 170° C.

EXAMPLE (IIIa-2)

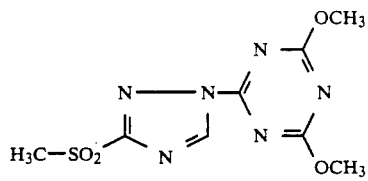

Chlorine gas is passed into a solution of 3 8 g (0.015 mol) of 2-(3-methylthio-1,2,4-triazol-l-yl)-4,6-dimethoxy-s-triazine in 25 ml of chloroform and 12.5 ml of water at 0° C. to 5° C. until the point of saturation, and the mixture is then stirred for 10 more minutes and subsequently diluted with 100 ml of chloroform and shaken with water. The organic phase is separated off, dried using sodium sulphate and filtered. The solvent is removed from the filtrate by distillation under a waterpump vacuum.

2.8 g (67% of theory) of 2-(3-methylsulphonyl1,2,4-triazol-1-yl)-4,6-dimethoxy-s-triazine are obtained as a crystalline residue of melting point 170° C.

The following is obtained analogously:

(IIIa-3)

H₃C—SO₂—[triazole]—N—[triazine with OC₂H₅, OC₂H₅]

Melting point: 98° C.

STARTING MATERIALS OF THE FORMULA (IIIc)

EXAMPLE (IIIc-1)

H₃C—S—[triazole]—N—[triazine with OCH₃, OCH₃]

A mixture of 8.75 g (0.05 mol) of 2-chloro-4,6-dimethoxy-s-triazine, 9.8 g (0.85 mol) of 3-methylthio1,2,4-triazole, 6.9 g (0.05 mol) of potassium carbonate and 100 ml of acetonitrile is refluxed for 20 hours. The mixture is subsequently evaporated, and the residue is taken up in 200 ml of methylene chloride and washed twice with 100 ml of water each time. The organic phase is dried using sodium sulphate and filtered. The solvent is removed from the filtrate by distillation under a water-pump vacuum.

11.7 g (92% of theory) of 2-(3-methylthio-1,2,4-triazol-1-yl)-4,6-dimethoxy-s-triazine are obtained as a crystalline residue of melting point 160° C.

The following is obtained analogously:

(IIIc-2)

H₃C—SO₂—[triazole]—N—[triazine with OC₂H₅, OC₂H₅]

Melting point: 157° C.

(IIIc-3)

H₃C—S—[triazole]—N—[triazine with OCH₃, OC₂H₅]

Melting point; 155° C.

Use Examples

Example A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example the compounds of Preparation Examples 1, 4, 8 and 12 show a powerful action against weeds, such as, for example, Datura, Galium, Polygonum, Sinapis, Veronica, Helianthus and Xanthium, while having a good seleclivily in wheat and corn.

It is understood that the specification and examples are illustrative but not limitative of the present invention and that other embodiments within the spirit and scope of the invention will suggest themselves to those skilled in the art.

We claim:

1. A sulphonylaminoazine of the formula

[Structure (I): substituted phenyl with $R^2$, $R^3$, $R^1$ connected via $(CH_2)_n$—$SO_2$—$NH$— to azine ring with X, Y, Z]

in which $R^1$ represents halogen, cyano, nitro, $C_1$-$C_2$-alkyl, $C_1$-$C_2$-halogenoalkyl, $C_1$-$C_2$-alkoxy, $C_1$-$C_2$-halogenoalkoxy, $C_1$-$C_2$-alkylthio, $C_1$-$C_2$-halogenoalkylthio, $C_1$-$C_2$-alkylsulphinyl, $C_1$-$C_2$-halogenoalkylsulphinyl, $C_1$-$C_2$-alkylsulphonyl, $C_1$-$C_2$-halogenoalkylsulphonyl, $C_1$-$C_2$-alkoxy-C-$C_2$-alkoxy, di-($C_1$-$C_2$-alkylamino)-sulphonyl, N-($C_1$-$C_2$-alkoxy)-N-($C_1$-$C_2$-alkyl)-aminosulphonyl or $C_1$-$C_2$-alkoxy-carbonyl, $R^2$ and $R^3$ independently of one another represent hydrogen, halogen, alkyl or halogenoalkyl, n represents the numbers 0 or 1, X represents hydrogen, $C_1$-$C_2$-alkyl, $C_1$-$C_2$-halogenoalkyl, $C_1$-$C_2$-alkoxy-$C_1$-$C_2$-alkyl, cyclopropyl, $C_1$-$C_2$-alkoxy, $C_1$-$C_2$-halogenoalkoxy, $C_1$-$C_2$-alkoxy-$C_1$-$C_2$-alkoxy, $C_1$-$C_2$-alkylthio, $C_1$-$C_2$-alkylamino or di-($C_1$-$C_2$-alkyl)-amino, and Y represents halogen, $C_1$-$C_2$-alkyl, $C_1$-$C_2$-halogenoalkyl, cyclopropyl, $C_2$-$C_2$-alkoxy, $C_1$-$C_2$-halogenoalkoxy or $C_1$-$C_2$-alkylthio, or a salt thereof.

2. A sulphonylaminoazine according to claim 1, in which $R^1$ represents fluorine, chlorine, bromine, iodine, cyano, nitro, methyl, trifluoromethyl, chlorodifluoromethyl, difluoromethyl, methoxy, ethoxy, difluoromethoxy, trifluoromethoxy, chlorodifluoromethoxy, 2-chloro-ethoxy, 1,1,2,2-tetrafluoroethoxy, 2-chloro-1,1,2-trifluoroethoxy, methylthio, ethylthio, difluoromethylthio, trifluoromethylthio, chlorodifluoromethylthio, methylsulphinyl, ethylsulphinyl, trifluoromethylsulphinyl, methylsulphonyl, ethylsulphonyl, trifluoromethylsulphonyl, 2-methoxy-ethoxy, 2-ethoxy-ethoxy, dimethylaminosulphonyl, N-methoxy-N-methylaminosulphonyl, methoxycarbonyl or ethoxycarbonyl, $R^2$ and $R^3$ independently of one another represent hydrogen, fluorine, chlorine, bromine, methyl or trifluoromethyl, n represents the numbers 0 or 1, X represents hydrogen, methyl, ethyl, trifluoromethyl, chloromethyl, methoxymethyl, cyclopropyl, methoxy, ethoxy, difluoromethoxy, 2,2,2-trifluoroethoxy, methoxy-methoxy, 2-methoxy-ethoxy, methylthio, methylamino, ethylamino or dimethylamino, and Y represents fluorine, chlorine, bromine, methyl, ethyl, trifluoromethyl, chloromethyl, cyclopropyl, methoxy, ethoxy, difluoromethoxy, 2,2,2-trifluoroethoxy, or methylthio, or a sodium or potassium salt thereof.

3. A sulphonylaminoazine or salt thereof according to claim 1, in which $R^1$ represents fluorine, chlorine, bromine, methyl, trifluoromethyl, difluoromethoxy, trifluoromethoxy, 2-chloro-ethoxy, methylthio, methylsulphonyl, dimethylaminosulphonyl, methoxycarbonyl or ethoxycarbonyl, $R^2$ represents hydrogen, fluorine or chlorine, $R^3$ represents hydrogen, n represents the numbers 0 or 1, X represents methyl, methoxy or ethoxy, and Y represents methyl, methoxy or ethoxy.

4. A compound according to claim 1, wherein such compound is 2-(2-chloro-phenyl-sulphonylamino)-4,6-dimethoxy-s-triazine of the formula

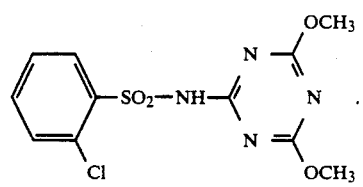

5. A compound according to claim 1, wherein such compound is 2-(2-fluoro-phenyl-sulphonylamino)-4,6-dimethoxy-s-triazine of the formula

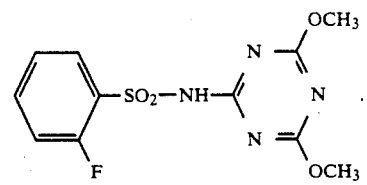

6. A compound according to claim 1, wherein such compound is 2-(2-methoxycarbonyl-phenyl-sulphonylamino)-4,6-diethoxy-s-triazine of the formula

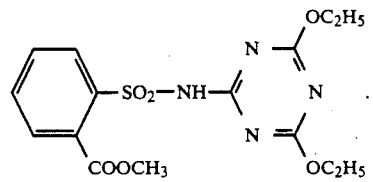

7. A compound according to claim 1, wherein such compound is 2-(2-difluoromethoxy-phenyl-sulphonylamino)-4,6-diethoxy-s-triazine of the formula

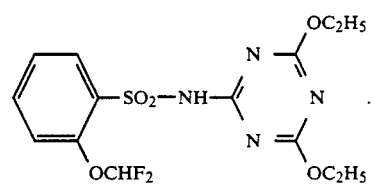

8. A herbicidal composition comprising a herbicidally effective amount of a sulphonylaminoazine according to claim 1 and a diluent.

9. A method of combating unwanted vegetation which comprises applying thereto or to a locus from which it is desired to exclude such vegetation a herbicidally effective amount of a compound according to claim 1.

10. The method according to claim 9, wherein such compound is 2-(2-chloro-phenyl-sulphonylamino)-4,6-dimethoxy-s-triazine, 2-(2-fluoro-phenyl-sulphonylamino)-4,6-dimethoxy-s-triazine, 2-(2-methoxycarbonyl-phenyl-sulphonylamino)-4,6-diethoxy-s-triazine or 2-(2-difluoromethoxy-phenyl-sulphonylamino)-4,6-diethoxy-s-triazine.

11. A compound of the formula

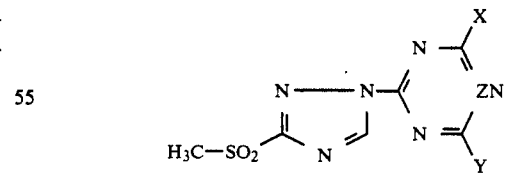

in which

X represents hydrogen, $C_1$-$C_2$-alkyl, $C_1$-$C_2$-halogenoalkyl, $C_1$-$C_2$-alkoxy-$C_1$-$C_2$-alkyl, cyclopropyl, $C_1$-$C_2$-alkoxy, $C_1$-$C_2$-halogenoalkoxy, $C_1$-$C_2$-alkoxy-$C_1$-$C_2$-alkoxy, $C_1$-$C_2$-alkylthio, $C_1$-$C_2$-alkylamino or di-($C_1$-$C_2$-alkyl)-amino, and Y represents halogen, $C_1$-$C_2$-alkyl, $C_1$-$C_2$-halogenoalkyl, cyclopropy, $C_2$-$C_2$-alkoxy, $C_1$-$C_2$-halogenoalkoxy or $C_1$-$C_2$-alkylthio.

* * * * *

UNITED STATES PATENT AND TRADEMARK OFFICE
CERTIFICATE OF CORRECTION

PATENT NO. : 5,006,156
DATED : April 9, 1991
INVENTOR(S) : Gesing et al.

It is certified that error appears in the above-identified patent and that said Letters Patent is hereby corrected as shown below:

On the title page:   ABSTRACT: Line 12 after " $C_1$- " delete " ( " , line 17 after " halogenoalkyl, " insert -- $C_1$-$C_2$-alkoxy --

Col. 16, claim 1 line 2   Delete " 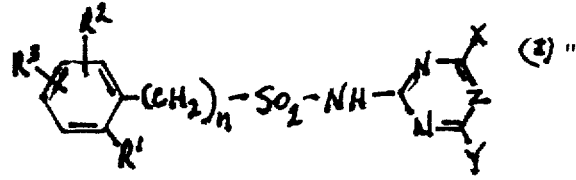 "

and substitute

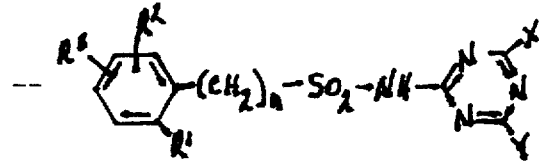   --

Col. 16, line 49   Delete " C-$C_2$-alkoxy " and substitute -- $C_1$-$C_2$-alkoxy --

Col. 18, claim 11 line 2   Delete " 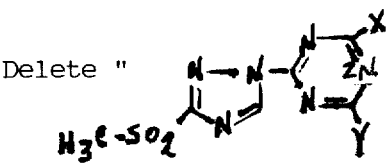 " and sub-

UNITED STATES PATENT AND TRADEMARK OFFICE
CERTIFICATE OF CORRECTION

PATENT NO. : 5,006,156

DATED : April 9, 1991

INVENTOR(S) : Gesing et al.

It is certified that error appears in the above-identified patent and that said Letters Patent is hereby corrected as shown below:

stitute -- 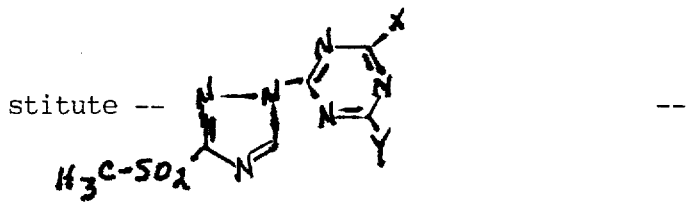 --

Signed and Sealed this

Sixth Day of April, 1993

*Attest:*

STEPHEN G. KUNIN

*Attesting Officer*    Acting Commissioner of Patents and Trademarks